United States Patent [19]

Marcotullio et al.

[11] Patent Number: 5,364,960
[45] Date of Patent: Nov. 15, 1994

[54] PROCESS FOR PREPARING SULFONATED PARAFFINS WITH A LARGER CONTENT OF POLYSULFONATED SPECIES

[75] Inventors: Armando Marcotullio, San Donato Milanese; Laura Tinucci, Cervignano D'Adda; Massimo Ciali, Milan, all of Italy

[73] Assignees: Eniricerche S.p.A.; Enichem Augusta Industriale S.r.l., both of Milan, Italy

[21] Appl. No.: 152,704

[22] Filed: Nov. 16, 1993

[30] Foreign Application Priority Data

Nov. 20, 1992 [IT] Italy ............... MI92 A 002659

[51] Int. Cl.$^5$ ............................ C07C 143/02
[52] U.S. Cl. ............................ 562/121
[58] Field of Search ..................... 562/121

[56] References Cited

U.S. PATENT DOCUMENTS 2,503,280  4/1950  Lockwood .
2,507,088  1/1948  Walton ................ 562/121
2,645,656  7/1953  Oldham et al. .
3,413,337  11/1968  Bost .................. 562/121
3,479,398  11/1969  Bost .................. 562/121
3,485,870  12/1969  Bost .................. 562/121
3,518,299  6/1970  Alston ................ 562/121
3,926,757  12/1975  Rosinger ............. 562/121
3,956,371  5/1976  Bjellqvist ........... 562/121
4,054,599  10/1977  Shuttleworth ........ 562/121
5,107,019  4/1992  Gallistru ........... 562/121

Primary Examiner—José G. Dees
Assistant Examiner—Samuel Barts
Attorney, Agent, or Firm—Oblon, Spivak, McClelland, Maier & Neustadt

[57] ABSTRACT

Process for obtaining sulfonated paraffins containing more than 50% of polysulfonates, by weight, by causing essentially linear $C_{12}$–$C_{20}$ paraffins to react with $SO_2$ and $O_2$, at a temperature comprised within the range of from 55 to 100° C. and in the presence of a peroxide belonging to the class of peroxy dicarbonates.

8 Claims, No Drawings

PROCESS FOR PREPARING SULFONATED PARAFFINS WITH A LARGER CONTENT OF POLYSULFONATED SPECIES

The present invention relates to a process for producing sulfonated paraffins with a large content of polysulfonates.

By "polysulfonate", paraffins are understood herein, which contain more than one sulfonic groups in their molecule, in other terms, compounds having the general formula $$C_nH_{2n+2-x}(SO_3Na)_x$$

wherein x is higher than 1.

By "paraffins", linear $C_{12}$–$C_{20}$ aliphatic hydrocarbons and their mixtures are understood, as, e.g., deriving from petroleum fractions dewaxing. Obviously, the above said linear paraffins may contain very small amounts of branched isomers or other impurities.

From pertinent technical literature, processes for sulfo-oxidating paraffins with $SO_2$ and $O_2$, in the presence of suitable catalysts, yielding useful sulfonates for use in detergency field, are well known. In particular, the process using U.V. light as catalyst has already been developed on the large industrial scale.

However, many other patents exist in technical literature which disclose sulfo-oxidation processes catalysed by gamma rays and free-radical generator substances.

So, e.g., U.S. Pat. No. 2,503,280 discloses using catalysts belonging to the class of alpha,alpha'-azobis(cyano alkanes).

U.S. Pat. No. 2,507,088 discloses a lead tetraacetate based catalyst.

U.S. Pat. No. 3,372,188 discloses a process carried out in the presence of compounds or of conditions capable of producing free radicals, such as U.V. light, gamma radiation, peroxides or azocompounds, by feeding $S_2$ and $O_2$ in the presence of $SO_3$.

Still other process variants are reported in U.S. Pat. No. 3,518,299 (sulfur dioxide, oxygen, sulfur trioxide and a lower amount of fatty acids) and in U.S. Pat. No. 3,485,870 (presence of halo-oxyacids or their salts).

All these processes, whether catalysed by U.V. light, gamma radiation or compounds capable of generating free radicals, prevailingly lead to monosulfonated products. As regards process catalysed gamma radiation, this is explicitly stated in European Chemical News, Jun. 14th, 1963, page 31; as regards the processes catalysed by free-radical initiators, this implicitly results from U.S. Pat. No. 2,507,088, wherein the inventor states that by starting from cetane (molecular weight=226), a sodium sulfonate with molecular weight=337 is obtained, versus a theoretical molecular weight for sodium cetane monosulfonate of 328.

On the other hand, the need is more and more felt, in particular in petroleum industry, of having available sulfonates which are stable in divalent-ions environments, which are often met in oil well drilling.

Such a feature cannot be achieved with mono-sulfonates which, in the presence of high concentrations of divalent ions, precipitate and consequently are ineffective.

This drawback is also confirmed by U.S. Pat. No. 5,031,698, which reports that in oil well drilling surfactant mixtures are advantageously used which derive from olefin sulfonation with $SO_3$, which leads to polysulfonate-rich product mixtures.

The present Applicants have found now a simple and cheap process which makes it possible to obtain sulfonated paraffins with a large amount of polysulfonates, by means of the oxidative sulfonation of paraffins under particular reaction conditions.

In accordance therewith, the present invention relates to a process for obtaining sulfonated paraffins containing more than 50% of polysulfonates, by weight, by causing essentially linear $C_{12}$–$C_{20}$, preferably $C_{14}$–$C_{17}$, paraffins or their mixtures to react with $SO_2$ and $O_2$, characterized in that said process is carried out at a temperature comprised within the range of from 55° to 100° C., preferably of from 60° to 95° C., the presence of a peroxide belonging to the class of peroxy dicarbonates, with the ratio of $SO_2$:paraffin, by weight, being higher than 0.9.

According to a preferred embodiment of the present invention, the ratio of $SO_2$:paraffin, by weight, is comprised within the range of from 0.8 to 1.3; in a still more preferred embodiment, said ratio is comprised within the range of from 0.9 to 1.2.

The paraffins to be used as substrate to be submitted to sulfonation preferably are mixtures of linear paraffins, with any non-linear isomers and other impurities being contained at levels of not more than 2% by weight.

By "$C_{12}$–$C_{20}$" or "$C_{14}$–$C_{17}$ paraffins", mixtures of paraffins having the above cited purity level are understood, which are prevailingly constituted by products containing a number of carbon atoms comprised within the range of from 12 to 20 and 14 to 17, respectively. In fact, the above said mixture usually contain, to a minor extent, also paraffins containing a number of carbon atoms outside of the indicated range, globally at lower levels than 20% by weight.

The sulfo-oxidation reaction (by means of this expression the reaction with $SO_2$ and $O_2$ being understood) of the paraffin mixture is catalysed by a free-radical generating initiator belonging to the class of peroxy dicarbonates, i.e., compounds having the general formula (I)

$$R-O-CO-O-O-CO-OR' \qquad (I)$$

wherein R and R', which may be the same or different from each other, are alkyl or cycloalkyl radicals.

According to the preferred embodiment of the present invention, the peroxy dicarbonate is bis(4-tert.-butyl-cyclohexyl)peroxy dicarbonate, referred to in the following, in short form, as "BTC".

The necessary amount of peroxide falling within the scope of the general formula (I) in order to catalyze the sulfo-oxidation reaction is comprised within the range of from 0.0001 to 0.03 parts per paraffin part, preferably of from 0.0006 to 0.02. Also larger amounts can be used, but in this case no further benefits are obtained in terms of yield and of ratio of polysulfonate to mono-sulfonate.

The reaction is carried out under such (temperature and pressure) conditions as to keep $SO_2$ prevailingly in liquid form.

When the process is carried out batchwise, the mixture of paraffins, peroxy dicarbonate, liquid $SO_2$ can be charged to the autoclave which is then pressurized with $O_2$. The autoclave is heated up to at least the peroxide decomposition temperature (about 55°–75° C.), with oxygen consumed by the reaction being replenished.

Once that the free-radical reaction is started, still operating batchwise, the reactor temperature should be controlled by suitable means for removing the reaction heat, e.g., by external water circulation.

The total reaction time is a function of temperature, of peroxide type and of the mutual reactants ratio. For example, in the presence of BTC peroxy dicarbonate and operating at a temperature comprised within the range of from 65° to 90° C., the reaction is complete within 70–120 minutes.

After discontinuing heating and venting off any unconverted $SO_2$, the raw reaction mixture is processed according to usual techniques: separation of the hydrocarbonaceous phase containing the unreacted paraffin from the aqueous phase containing the sulfonated product, and neutralization of the aqueous phase with alkali metal or ammonium hydroxides, preferably with aqueous NaOH.

The resulting paraffin sulfonate has a sulfonation degree, expressed as the index "x" in the general formula $$C_nH_{2n+2-x}(SO_3Na)_x$$

decidedly higher than 1, usually comprised within the range of from 1.4 to 1.8.

The so obtained paraffin sulfonate has a composition (from the viewpoint of the ratio of mono-sulfonate to polysulfonate) which renders it useable, with no further separations or purifications, as a foaming agent in a strongly ionic medium and in sea water. This property, together with its easy preparation, makes it particularly useful as a foaming agent in oil well drilling and exploitation, a field in which high-salinity conditions are often met.

The following examples are reported in order to better illustrate the present invention.

EXAMPLES

In order to prepare the paraffin sulfonate according to the present invention, a mixture of n-paraffins having the following characteristics is used:
Composition:
  $<C_{13}=0.2\%$;
  $C_{13}=3\%$;
  $C_{13}+C_{14}+C_{15}=65.2\%$;
  $C_{16}+C_{17}=32\%$;
  $>C_{17}=1.7\%$;
Average molecular weight=212.5;
Initial boiling point (under 1.013 bars)=249° C.;
End boiling point (same pressure)=300° C.;
Total paraffin content: 99.1%;
Density at 15° C.; 0,772 kg/L.

Example 1

To a pressure resistant autoclave of 5 liters of capacity equipped with magnetic stirring means and provided with four valves, one of which is connected with a dip tube, thermometer well, with a pressure gauge suitable for corrosive fluids and with a pressure relief valve (PSV), 1,604.4 g of $C_{14}$–$C_{17}$ paraffin and 1,2570 g of (4-tert.-butyl-cyclohexyl)peroxy dicarbonate are loaded under open-top autoclave conditions, the autoclave is closed and 1,490 g of $SO_2$ is added. The autoclave is pressurized with oxygen up to a total pressure of 22 kg/cm$^2$, is heated from 9° up to 68° C. during 48 minutes, and at approximately 68° C. the reaction is started. The temperature, controlled by means of cooling water flowing inside the external autoclave coil, is kept comprised within the range of from 68° to 82° C., with consumed oxygen being replenished up to 37.5 kg/cm$^2$. The maximal temperature after reaction starting results to be of 82° C. Then, the reactor is kept at a temperature comprised within the range of from 80° to 90° C. and, after 120 minutes, the autoclave heating and stirring are discontinued and $SO_2$ is vented off, through an aqueous sodium hydroxide solution.

After purging a plurality of times with nitrogen, the autoclave is opened; the reaction product is recovered and is transferred to a separator funnel in which the phase separation takes place.

The upper phase, containing the unreacted paraffin, is washed with two portions of 300 ml each of water in order to recover any possibly absorbed sulfonic acid. The bottom phase, containing the paraffin sulfonic acid and combined with the water washes of the upper phase, is neutralized under pH control, with 456 g of an aqueous sodium hydroxide solution at 20% by weight.

The neutralized aqueous solution is extracted with n-heptane in order to recover the dissolved paraffin in micellar phase.

The upper phase, combined with the heptanic extracts, is concentrated on a rotary evaporator at 80° C. and 20 torr, until constant weight, with any unreacted paraffin being recovered. The paraffin conversion rate results to be of 12.3%.

The neutralized and refined aqueous solution is freeze-dried with 323.7 g being recovered of a raw product having the following composition:
* $H_2O=1.82\%$;
* $Na_2SO_4=17.58\%$;
* organic sodium sulfonate=80.6%.

By $^{13}C$-NMR analysis, the sulfonation degree, i.e., the x value in the formula $$C_nH_{2n+2-x}(SO_3Na)_x$$

of the resulting sulfonate, is determined: it results to be of 1.58.

Example 2

By using a 1-liter autoclave, 389.3 g of n-($C_{14}$–$C_{17}$)-paraffins and 0.2464 of (4-tert.-butyl-cyclohexyl)-peroxy dicarbonate are charged. A seal tightness test is carried out with $N_2$, 410 g of liquid $SO_2$ is charged and the autoclave is pressurized with oxygen (temperature about 11° C.), total pressure: 11 kg/cm$^2$).

Within a time of approximately 23 minutes, the temperature is increased up to 69° C.; at this temperature value, the reaction is started. Although heating is discontinued at that time and cooling the autoclave is started by circulating water through the external jacket, the temperature increases up to about 73°–74° C., then remains at this value fop approximately 45 minutes. During this time period, owing to sulfonation, the pressure of 02 decreases, so the initial pressure value of about 20 kg/cm$^2$ is restored by means of 6 sequential oxygen additions.

At this time the stirrer is stopped, any residual $SO_2$ is vented off, the autoclave is accurately purged with nitrogen, and the product is then recovered, with autoclave being washed with heptane and water.

The product is discharged and is trasnferred to a separator funnel of 2 liters of capacity and then the resulting phases are separated from each other. The top phase, which contains heptane and unreacted paraffin, is washed with a portion of water, which is recovered and combined with the preceding aqueous phase.

The whole aqueous phase is then neutralized with an aqueous solution at 20.5% of NaOH; in order to adjust the pH value of the aqueous sulfonate solution at about 9, 361.2 g of said solution is consumed.

In order to purify the aqueous solution of sodium sulfonate from any traces of unreacted paraffin, said solution about 300 ml of isopropanol is added. The mixture is then extracted with heptane until paraffin is totally disappeared.

All heptanic extracts are combined and concentrated to dryness; in that way, 269.4 g of unreacted paraffin is recovered.

The sulfonated paraffin containing aqueous phase is freeze-dried, and 296.2 g is recovered of a solid which is constituted by:
* $H_2O = 2.54\%$;
* $Na_2SO_4 = 17.89\%$;
* active portion: 79.57%.

The paraffin conversion rate was hence of 30.8% by weight.

The active portion resulted to be composed (by N.M.R. analysis) by 30% by weight by mono-sulfonated paraffin and 70% by weight by polysulfonated paraffin.

Example 3

2.0 g of sodium salt resulting from the preparation disclosed in Example 2 (30% mono-sulfonate, 70% polysulfonate) is added to 100 ml of an aqueous solution containing 10% of calcium chloride (corresponding to a concentration of $Ca^{++}$ ions of 3.6% by weight). The resulting, slightly hazy solution, is filtered and the filtrate, analysed by HPLC., results to be constituted by 0.3 g of mono-sulfonate and 1.4 g of di-sulfonate.

2.0 g of said sulfonate is added to an aqueous solution containing 10% of magnesium chloride (corresponding to a concentration of $Mg^{++}$ ions of 2.6% by weight). The resulting, perfectly clear, solution, is filtered and the filtrate, analysed by HPLC., results to have the same starting composition.

2.0 g of said sulfonate is added to an aqueous solution of synthetic sea water ($CaCl_2$ 0.1%, $MgCl_2$ 0.5%, $NaHC_3$ 0.02%, $Na_2SO_4$ 4.0%, NaCl 2.4%). The resulting, perfectly clear, solution is filtered and the filtrate, analysed by HPLC., results to have the starting composition.

These tests evidence the stability of the mixture of sulfonated paraffins prepared according to the process disclosed hereinabove, to sea water and magnesium ions. Only at high concentrations of calcium ions, a small amount of mono-sulfonated paraffin precipitates.

Example 4

(Comparison Example)

For comparison purposes, 2.0 grams of sodium paraffin sulfonate derived from the sulfonation on pilot scale of the same paraffins as used in Examples 1 and 2, but by means of a process catalysed by U.V. light (composition: 90% mono-sulfonate and 10% poly-sulfonate) is added to 100 ml of an aqueous solution at 10% of $CaCl_2$. A precipitate is formed and is filtered off. By HPLC analysis, the amount and the type of sulfonate remained in solution is determined; it results to be 0.2 g of polysulfonate.

Example 5

With this example, the high foaming power of sodium salt of sulfonated paraffin prepared according to as disclosed in Example 2, is demonstrated.

The foaming power in deionized water in synthetic sea water was determined by means of the ASTM method D 1173-53 by Ross Miles, both at room temperature and at 50° C.

The results obtained (Table 1) for a concentration of product of Example 2, of 3 g/l, evidence a high foaming power both in deionized water and in synthetic sea water, at room temperature and at 50° C.

In table 1, the headings "h 0 min", "h 5 min". "h 10 min" are the height of foam expressed as cm at time 0, or after 5 and 10 minutes, respectively.

TABLE 1

| Type of $H_2O$ | Temp. °C. | h 0 min (cm) | h 5 min (cm) | h 10 min (cm) |
|---|---|---|---|---|
| Deionized water | 25 | 154 | 148 | 146 |
| Sea water | 25 | 110 | 110 | 100 |
| Sea water | 50 | 160 | 160 | 145 |

In Table 2 also the data is reported for comparison purposes, which relates to the mixture of sodium salts of sulfonated paraffins obtained from a pilot facility, by starting from the same paraffins, by catalysis with U.V. light. The same concentrations and the same conditions as reported in Table 1 were used.

TABLE 2

| Type of $H_2O$ | Temp. °C. | h 0 min (cm) | h 5 min (cm) | h 10 min (cm) |
|---|---|---|---|---|
| Deionized water | 25 | 155 | 152 | 140 |
| Sea water | 25 | 60 | 50 | 43 |
| Sea water | 50 | 80 | 80 | 70 |

When the data reported in Table 1 is compared to the data of Table 2, it can be observed that the sulfonated paraffins prepared according to the process of the present invention are much more effective, in the presence of divalent ions, than the corresponding sulfonated paraffins prepared by means of a catalysis with U.V. light.

We claim:

1. A process for preparing a sulfonated paraffin comprising more than 50% by weight of polysulfonates, said process comprising contacting an essentially linear $C_{12}$-$C_{20}$ paraffin or a mixture of essentially linear $C_{12}$-$C_{20}$ paraffins with $SO_2$ and $O_2$, wherein said contacting is carried out at a temperature within the range of from 55° to 100° C. in the presence of a peroxy dicarbonate having the formula (I)

$$-R-O-CO-O-O-CO-O-R' \qquad (I)$$

wherein R and R', which may be the same or different, are alkyl or cycloalkyl radicals, with a ratio of $SO_2$:-paraffin, by weight, being higher than 0.8.

2. Process according to claim 1, characterized in that the ratio of $SO_2$:paraffin, by weight, is within the range of from 0.8 to 1.3.

3. Process according to claim 2, characterized in that the ratio of $SO_2$:paraffin, by weight, is within the range of from 0.9 to 1.2.

4. Process according to claim 1, characterized in that the reaction temperature is within the range of from 60° to 95° C.

5. Process according to claim 1, characterized in that the peroxy dicarbonate is bis(4-tert.-butyl-cyclohexyl)-peroxy dicarbonate.

6. Process according to claim 1, characterized in that the amount of peroxy dicarbonate of formula (I) is within the range of from 0.0001 to 0.03 parts per paraffin part.

7. Process according to claim 6, characterized in that the amount of peroxy dicarbonate of formula (I) is within the range of from 0.0006 and 0.02 parts per paraffin part.

8. The process according to claim 1, wherein said linear $C_{12}$–$C_{20}$ paraffin or mixture of linear $C_{12}$–$C_{20}$ paraffins is a linear $C_{14}$–$C_{17}$ paraffin.

* * * * *